United States Patent [19]

Novy

[11] Patent Number: 4,965,366
[45] Date of Patent: Oct. 23, 1990

[54] METHOD FOR PRODUCING 1-(TRISUBSTITUTED SILYL)AZOLES

[75] Inventor: Paul M. Novy, Roselle, Ill.

[73] Assignee: PPG Industries, Inc., Pittsburgh, Pa.

[21] Appl. No.: 608,006

[22] Filed: May 7, 1984

[51] Int. Cl.$^5$ .......................................... C07D 231/00
[52] U.S. Cl. .................................................... 548/110
[58] Field of Search ......................................... 548/110

[56] References Cited

U.S. PATENT DOCUMENTS

| | | | |
|---|---|---|---|
| 3,373,137 | 3/1968 | Saam | 548/110 |
| 3,809,713 | 5/1974 | Boersma et al. | 260/448.2 E |
| 3,847,917 | 11/1974 | Vorbruggen | 548/110 |
| 4,273,709 | 6/1981 | Christensen | 260/239 A |
| 4,518,787 | 5/1985 | Treadgold | 556/442 |

OTHER PUBLICATIONS

M. Ogata et al, "N-(Chlorosulfinyl)-Imidazole as a New Imidazole Transfer Agent", *Synthetic Communications*, vol. 10, No. 10, 1980, pp. 733-742.

W. Foerst, *Newer Methods of Preparative Organic Chemistry*, vol. V, Academic Press, New York (1968), pp. 61-108 and 211-237 [H. A. Staab and W. Rohr, "Syntheses Using Heterocyclic Amides (Azolides)"; L. Birkofer and A. Ritter, The Use of Silylation in Organic Syntheses].

B. E. Cooper, "Silylation as a Protective Method in Organic Synthesis", Chemistry and Industry, Oct. 21, 1978, pp. 794-797.

V. D. Sheludyakov et al, "Reactions of N-(Trimethylsilyl) Derivatives..." Translation from *Zhurnal Obschei Khimii*, vol. 50, No. 4, pp. 875-881, Apr. 1980, Translation Published 1980, pp. 705-711.

Primary Examiner—Peter F. Kulkosky
Attorney, Agent, or Firm—George D. Morris

[57] ABSTRACT

1-Unsubstituted 1H-azole compound, halo trisubstituted silane, and primary amine are reacted to form 1-(trisubstituted silyl)-1H-azole compound which principally accumulates in a liquid phase and hydrohalide salt of the primary amine which principally accumulates in at least one phase different from the liquid phase. In the preferred embodiment, the 1-(trisubstituted silyl)-1H-azole compound so produced is further reacted to produce one or more products and to regenerate the halo trisubstituted silane which is recycled to the earlier reaction.

21 Claims, 1 Drawing Sheet

METHOD FOR PRODUCING 1-(TRISUBSTITUTED SILYL)AZOLES 1-(Trisubstituted silyl)-1H-azole compounds are useful intermediates in the preparation of many compounds, including antibiotics, peptides, esters, amides, hydrazides, hydroxamic acids, acyl chlorides, aldehydes, peroxides, ketones, ureas, and other compounds. See for example, W. Foerst, *Newer Methods of Preparative Organic Chemistry*, Volume V, Academic Press, New York (1968) pages 211–237 [L. Birkofer and A. Ritter, "The Use of Silylation in Organic Syntheses"] and pages 61–108 [H. A. Staab and W. Rohr, "Syntheses Using Heterocyclic Amides (Azolides)"] and U.S. Pat. No. 4,273,709. The Birkofer and Ritter paper shows the use of 1-(trisubstituted silyl compounds) in forming many compounds, among which are the 1,1'-carbonylbis(1H-azole) compounds. The Staab and Rohr paper and U.S. Pat. No. 4,273,709 show the use of 1,1'-carbonylbis(1H-azole) compounds in preparing many of the types of compounds mentioned above, of which antibiotics and peptides are especially noteworthy examples.

A new method has been discovered for producing 1-(trisubstituted silyl)-1H-azole compounds. Accordingly, one aspect of the invention is the method comprising reacting (a) at least one 1-unsubstituted 1H-azole compound selected from 1-unsubstituted monocyclic 1H-diazole compounds, 1-unsubstituted bicyclic 1H-diazole compounds containing a fused benzene ring, 1-unsubstituted monocyclic 1H-triazole compounds, and 1-unsubstituted bicyclic 1H-triazole compounds containing a fused benzene ring, (b) at least one substituted silane represented by the formula $R_1R_2R_3SiX$, and (c) at least one primary amine, to form at least one 1-$(R_1R_2R_3Si)$ substituted 1H-azole compound which principally accumulates in a liquid phase and to form hydrohalide salt of the primary amine which principally accumulates in at least one phase which is different from the liquid phase in which the substituted 1H-azole compound principally accumulates, wherein $R_1$, $R_2$, and $R_3$ are each independently lower alkyl or phenyl and wherein X is fluoro, chloro, bromo, or iodo.

The multiphase system in which the reaction products are distributed is a distinct advantage of the present invention inasmuch as it permits considerably more facile separation of the products than if they were allowed to accumulate in a single phase.

The 1-unsubstituted 1H-azole compound contains but one secondary amino group,

and this is located in the 1-position of the azole ring. The compound is often unsubstituted at the other positions of the molecule; however it may be substituted in any of the other positions for which substitution is available, by substituents which do not preclude the desired reaction at the 1-position. Examples of substituents that may be used include lower alkyl and halo. Typically, the lower alkyl contains from 1 to 4 carbon atoms and the halo is chloro or bromo.

Examples of 1-unsubstituted 1H-azole compounds that may be used in this aspect of the invention include 1H-imidazole, 1H-pyrazol, 3,5-dimethyl-1H-pyrazole, 1H-1,2,4-triazole, 1H-benzimidazole, 1H-indazole and 1H-benzotriazole. 1H-Imidazole, 1H-1,2,4-triazole, 3,5-dimethyl-1H-pyrazole, 1H-benzimidazole, and 1H-benzotriazole are preferred. 1H-Imidazole is especially preferred. Only one 1-unsubstituted 1H-azole compound or a plurality of such compounds may be used as desired.

When any of $R_1$, $R_2$, or $R_3$ is lower alkyl, it usually contains from one to four carbon atoms. Methyl, ethyl, and tertiary butyl are the lower alkyl groups most often used. The preferred substituted silane is trimethylchlorosilane; consequently the preferred 1-$(R_1R_2R_3Si)$ substituted 1H-azole compounds are the 1-(trimethylsilyl)-1H-azole compounds. Only one substituted silane or a plurality of substituted silanes may be employed.

The primary amine may be any primary amine the hydrohalide salt of which principally accumulates in at least one phase different from the liquid phase in which the 1-$(R_1R_2R_3Si)$ substituted 1H-azole compound principally accumulates. Ordinarily, the hydrohalide salt principally accumulates in a single phase different from the liquid phase in which the 1-$(R_1R_2R_3Si)$ substituted 1H-azole compound principally accumulates. The different phase may be a liquid phase or it may be a solid phase, but a solid phase is preferred. However, if the reaction is conducted in the presence of an immiscible solvent in which the hydrohalide salt preferentially accumulates, and if that phase becomes saturated, it is believed that a further solid phase may form.

In general, the process is favored by employing a primary amine of which a hydrohalide salt is highly insoluble in the reaction mixture.

Of the primary amines, diaminoalkanes are most often used. The alkane portion may be straight or branched. Examples of straight chain diaminoalkanes include the $\alpha,\omega$-diamino-n-alkanes having from 2 to about 12 carbon atoms. From 2 to about 4 carbon atoms are preferred. An example of a branched diaminoalkane which may be employed is 1,2-diaminopropane. The preferred diaminoalkane is 1,2-diaminoethane. Only one primary amine or a plurality of primary amines may be used as desired.

The reaction may be conducted neat, but it is preferably conducted in the presence of inert solvent, the identity of which may vary considerably. Examples of inert solvents which may be used include methylene chloride, toluene, benzene, xylene, chlorobenzene, 1,2-dichloroethane, ethylacetate, tetrahydrofuran, 1,2-dimethoxyethane, and 1,4-dioxane. The preferred inert solvents are methylene chloride and toluene. Only one inert solvent or a plurality of inert solvents may be employed, as desired.

The reactants may be introduced to the reaction mixture in any order. They may be introduced concurrently or sequentially. The addition may be continuous or intermittent. In one preferred embodiment the substituted silane is introduced to a solution comprising the 1-unsubstituted 1H-azole compound and the primary amine. In another preferred embodiment, at least some of the substituted silane is introduced to a solution comprising the 1-unsubstituted 1H-azole compound before the primary amine is introduced. In yet another preferred embodiment, 1-unsubstituted 1H-azole compound and primary amine are introduced concurrently, usually but not necessarily, as separate streams to a solution comprising substituted silane.

The reaction is usually conducted in the liquid phase. It may be carried out batchwise, continuously, semi-batchwise or semicontinuously.

The temperatures at which the reaction is conducted may vary considerably, but ordinarily they are in the range of from about −10° C. to about +100° C. Temperatures in the range of from about 25° C. to about 70° C. are preferred.

The pressures at which the reaction is conducted are also subject to wide variation. Atmospheric and slightly superatmospheric pressures are generally employed, although greater or lesser pressures may be used. Generally the pressure is in the range of from about zero to about 1100 kilopascals, gauge. Preferably the pressure is in the range of from about zero to about 110 kilopascals, gauge.

The molar ratio of the substituted silane to the 1-unsubstituted 1H-azole compound introduced to the reaction is susceptible to wide variation, but typically it is in the range of from about 0.5:1 to about 4:1. Often the molar ratio is in the range of from about 1:1 to about 4:1. A molar ratio in the range of from about 1:1 to about 1.2:1 is preferred.

The equivalent ratio of the primary amine to the 1-unsubstituted 1H-azole compound introduced to the reaction may likewise be widely varied. Ordinarily the equivalent ratio is in the range of from about 0.5:1 to about 2:1. Often the equivalent ratio is in the range of from about 1:1 to about 2:1. An equivalent ratio in the range of from about 1:1 to about 1.2:1 is preferred.

When inert solvent is used, the weight ratio of inert solvent to the 1-unsubstituted 1H-azole compound initially present is subject to wide variation. The weight ratio of inert solvent, when used, to the 1-unsubstituted 1H azole compound initially present is usually in the range of from about 0.1:1 to about 20:1. From about 0.5:1 to about 4:1 is preferred.

The 1-($R_1R_2R_3$Si) substituted 1H-azole compound produced by the above process is a 1-($R_1R_2R_3$Si) substituted monocyclic 1H-diazole compound, a 1-($R_1R_2R_3$Si) substituted bicyclic 1H-diazole compound containing a fused benzene ring, a 1-($R_1R_2R_3$Si) substituted monocyclic 1H-triazole compound, or a 1-($R_1R_2R_3$Si) substituted bicyclic 1H-triazole compound containing a fused benzene ring. Broadly, the 1-($R_1R_2R_3$Si) substituted 1H-azole compound may contain a plurality of $R_1R_2R_3$Si- groups, but ordinarily it contains only one $R_1R_2R_3$Si- group. Examples of such 1-($R_1R_2R_3$Si) substituted 1H-azole compounds include 1-(trimethylsilyl)-1H-imidazole, 1-triethylsilyl)-1H-imidazole, 1-(triphenylsilyl)-1H-imidazole, 1-(tert-butyldimethyl)-1H-imidazole, 1-(trimethylsilyl)-1H-pyrazole, 1-(trimethylsilyl)-3,5-dimethyl-1H-pyrazole, 1-(trimethylsilyl-1H-1,2,4-triazole, 1-(dimethylethyl-silyl)-1H-1,2,4-triazole, 1-(trimethylsilyl)-1H-benzimidazole, 1-(tripropylsilyl)-1H-benzimidazole, 1-(trimethylsilyl)-1H-indazole, 1-(trimethylsilyl)-1H-benzotriazole and 1-(tributylsilyl)-1H-benzotriazole. The preferred 1-($R_1R_2R_3$Si) substituted 1H-azole compounds produced by the method are the 1-(trimethylsilyl) substituted 1H-azole compounds. 1-(Trimethylsilyl)-1H-imidazole, 1-(tert-butyldimethyl)-1H-imidazole, 1-(trimethylsilyl)-1H-1,2,4-triazole, 1-(trimethylsilyl)-3,5-dimethyl-1H-pyrazole, 1-(trimethylsilyl)-1H-benzimidazole and 1-(trimethylsilyl)-1H-benzotriazole are particularly preferred. 1-(Trimethylsilyl)-1H-imidazole is especially preferred.

Following the reaction, the liquid phase in which the 1-($R_1R_2R_3$Si) substituted 1H-azole compound has principally accumulated may be substantially separated from the different phase or phases in which the hydrohalide salt of the primary amine has principally accumulated, by any phase separation technique known to the art. Examples of such techniques include centrifugation and decantation, and in the case where a solid phase is involved, filtration. The 1-($R_1R_2R_3$Si) substituted 1H-azole compound may be recovered from the liquid phase by any of the various techniques known to the art. Evaporation of volatile liquids from the less volatile product is one technique sometimes employed. Precipitation of the product using a liquid in which the product is poorly soluble but in which most other components of the liquid phase are soluble, is another technique sometimes employed. It is preferred, however, to employ the liquid phase of the reaction mixture as feed stock to one or more further reactions in which the 1-($R_1R_2R_3$Si) substituted 1H-azole compound is converted to one or more other products.

The method described above is particularly advantageous when incorporated in a cyclic process in which at least some of the 1-($R_1R_2R_3$Si) substituted 1H-azole compound produced is further reacted to produce one or more products and to regenerate the substituted silane which is recycled to the earlier reaction. Accordingly, another aspect of the invention is a cyclic process comprising (a) reacting, in the presence of inert solvent, (i) at least one 1-unsubstituted 1H-azole compound selected from 1-unsubstituted monocyclic 1H-diazole compounds, 1-unsubstituted bicyclic 1H-diazole compounds containing a fused benzene ring, 1-unsubstituted monocyclic 1H-triazole compounds, and 1-unsubstituted bicyclic 1H-triazole compounds containing a fused benzene ring, (ii) at least one substituted silane represented by the formula $R_1R_2R_3$SiX, and (iii) at least one primary amine, to form at least one 1-($R_1R_2R_3$Si) substituted 1H-azole compound which principally accumulates in a liquid phase and to form hydrohalide salt of the primary amine which principally accumulates in at least one phase which is different from the liquid phase, (b) substantially separating the liquid phase from the different phase or phases, (c) reacting at least a portion of the 1-($R_1R_2R_3$Si) substituted 1H-azole compound or compounds with at least one member of the group consisting of

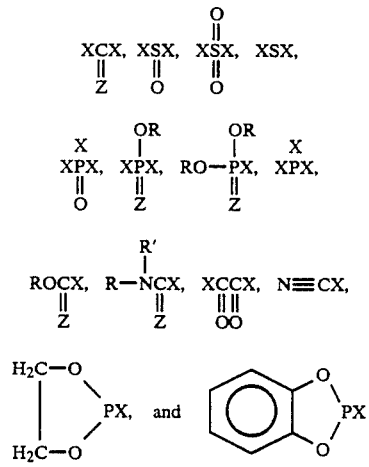

to form a reaction mixture comprising the inert solvent, the substituted silane, and material selected from (1) product compound formed by the replacement of at least one X of the member with a 1H-azol-1-yl group, (2) dissociation products of the product compound, and (3) a mixture thereof, (d) substantially separating the substituted silane produced in step (c) from the product compound or at least one dissociation product of the product compound, and (e) recycling the separated substituted silane to the reaction of step (a), wherein: $R_1$, $R_2$, and $R_3$ are each independently lower alkyl or phenyl; each R is independently lower alkyl, unsubstituted phenyl, phenyl substituted by from 1 to 3 halo groups, phenyl substituted by from 1 to 3 lower alkyl groups, ortho-nitrophenyl, para-nitrophenyl; each R' is independently hydrogen or R; each Z is independently oxygen or sulfur; and each X is independently fluoro, chloro, or bromo.

It is preferred that the hydrohalide salt principally accumulates in a solid phase and that the product comprises at least one compound in which each X of substantially all of the member has been replaced with a 1H-azol-1-yl group.

The earlier discussions in respect of $R_1$, $R_2$, $R_3$, R, R', Z, the 1-unsubstituted 1H-azole compound, the substituted silane, the primary amine, the inert solvent, the molar ratio of the substituted silane to the 1-unsubstituted 1H-azole compound introduced to the reaction, the equivalent ratio of the primary amine to the 1-unsubstituted 1H-azole compound introduced to the reaction, the weight ratio of the inert solvent to the 1-unsubstituted 1H-azole compound initially present, and the temperatures and pressures at which the reaction between 1-unsubstituted 1H-azole compound and substituted silane is conducted are all applicable to this aspect of the invention.

When R is lower alkyl, it typically contains from 1 to about 4 carbon atoms; methyl is preferred. Similarly, when R is phenyl substituted by from 1 to 3 lower alkyl groups, each lower alkyl group usually contains from 1 to about 4 carbon atoms; the preferred lower alkyl group in such cases is methyl. When R is phenyl substituted by from 1 to 3 halo groups, each halo is independently chloro or bromo.

R' may be hydrogen or any of the groups suitable for R. The 1-($R_1R_2R_3$Si) substituted 1H-azole compound produced and utilized as an intermediate in this aspect of the invention contains only one $R_1R_2R_3$Si— group. The compound is often unsubstituted at the other Positions of the molecule; however it may be substituted in any of the other positions for which substitution is available, by substituents which do not preclude the desired reaction at the 1-position. Examples of substituents that may be used include lower alkyl and halo. Only one 1-($R_1R_2R_3$Si) substituted 1H-azole compound or a plurality of such compounds may be produced and used as desired.

Examples of the members which may be reacted with the 1-($R_1R_2R_3$Si) substituted 1H-azole compound or compounds in the second reaction include phosgene, bromophosgene, bromochlorophosgene, fluorophosgene, thiophosgene, thionyl chloride, sulfuryl chloride, sulfur dichloride, phosphorous oxychloride, methyl dichlorophosphate, ethyl dibromophosphate, phenyl dichlorophosphate, ethyl dichlorothiophosphate, diethyl chlorophosphate, diphenyl chlorophosphate, dimethyl chlorothiophosphate, diethyl chlorothiophosphate, phosphorous trichloride, phosphorous tribromide, methyl chloroformate, ethyl chloroformate, butyl chloroformate, phenyl chloroformate, phenyl chlorothionocarbonate, methylcarbamyl chloride, phenylcarbamyl chloride, dimethylcarbamyl chloride, diphenylcarbamyl chloride, dimethylthiocarbamoyl chloride, cyanogen chloride, ethylene chlorophosphite, and o-phenylene chlorophosphite. Of the halogen-containing compounds with which the 1-($R_1R_2R_3$Si) substituted 1H-azole compound or compounds is/are reacted in the second reaction, the carbonic dihalides constitute a preferred subclass. Examples of carbonic dihalides which may be employed include phosgene, bromophosgene, bromochlorophosgene, and fluorophosgene. Phosgene is preferred.

The reactants for the second reaction may be introduced in any order. They may be introduced concurrently or sequentially. The introduction may be continuous or intermittent. In one embodiment a solution of the 1-($R_1R_2R_3$Si) substituted 1H-azole compound in the inert solvent is introduced to the halogen-containing member. In a preferred embodiment the halogen-containing member is introduced to a solution of the 1-($R_1R_2R_3$Si) substituted 1H-azole compound in the inert solvent. In another preferred embodiment a stream of the halogen-containing member and a stream of a solution of the 1-($R_1R_2R_3$Si) substituted 1H-azole compound in the inert solvent are introduced simultaneously.

The second reaction is conducted in the liquid phase. It may be carried out batchwise, continuously, semi-batchwise or semicontinuously.

The temperatures at which the second reaction is conducted may vary considerably, but ordinarily they are in the range of from about $-10°$ C. to about $+100°$ C. Temperatures in the range of from about 0° C. to about 60° C. are preferred.

The pressures at which the second reaction is conducted are also subject to wide variation. Atmospheric and slightly superatmospheric pressures are generally employed, although greater or lesser pressures may be used. Generally the pressure is in the range of from about 0 to about 1100 kilopascals, gauge. Preferably the pressure is in the range of from about 0 to about 110 kilopascals gauge.

The equivalent ratio of the halogen-containing member or members to the 1-($R_1R_2R_3$Si) substituted 1H-azole compound or compounds introduced to the reaction is susceptible to wide variation, but usually it is in the range of from about 0.2:1 to about 4:1. An equivalent ratio in the range of from about 0.9:1 to about 1.1:1 is preferred.

The weight ratio of inert solvent to the 1-($R_1R_2R_3$Si) substituted 1H-azole compound initially present is similarly subject to wide variation. The weight ratio of inert solvent to the 1-($R_1R_2R_3$Si) substituted 1H-azole compound initially present is usually in the range of from about 0.1:1 to about 20:1. From about 0.5:1 to about 4:1 is preferred.

In some instances the reaction product in which at least one X of the member has been replaced with a 1H-azol-1-yl dissociates into further products. In this case at least one of the dissociation products may be separated from the residuum of the reaction mixture. An example is the reaction product

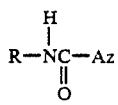

where Az is 1H-azol-1-yl, which is believed to dissociate according to the equation

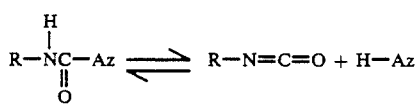

Either the isocyanate or the 1-unsubstituted 1H-azole compound or both may be separated from the residuum of the reaction mixture.

The product compound or at least one dissociation product of the product compound may be recovered from the reaction mixture by any of the techniques known to the art. In many cases the product compound precipitates from the reaction mixture during the reaction. Precipitation may ordinarily be enhanced by cooling the reaction mixture after the reaction is completed. The bulk of the precipitated product compound may be separated from the residuum of the reaction mixture, typically by filtration, centrifugation, or decantanation. The substituted silane may be recovered from the residuum of the reaction mixture by distillation prior to recycling. However, the residuum of the reaction mixture may be recycled without further separation.

Preferably the substituted silane is recovered from the reaction mixture by distillation. The distillation is often, but not necessarily, conducted under vacuum. The absolute pressure at which the distillation is conducted may vary widely, but typically it is in the range of from about 1 to about 400 kilopascals. An absolute pressure in the range of from about 10 to about 200 kilopascals is preferred. It is preferred to employ a distillation column providing more than one theoretical stage of distillation, although in those cases where the volatilities of substituted silane and solvent differ widely, simple distillation may be used. Typically the number of theoretical stages used is in the range of from more than one to about ten, although the maximum number is limited only by economic or practical physical considerations. The recovered substituted silane is recycled to the first reaction. Often during the distillation, product compound which may have precipitated dissolves in the solvent which remains in the bottoms.

After most of the substituted silane has been removed, the remaining solution or slurry, as the case may be, is stripped of solvent and the solid product compound which remains is dried. The pressures at which stripping and drying are conducted may also vary widely. Usually, but not necessarily, these operations are conducted under vacuum in order to maintain the temperature low enough to preclude untoward thermal degradation of the product. The recovered solvent may be used for any desired purpose but it is preferably recycled to the first reaction.

For a better understanding of the invention, reference may be made to the drawings wherein like numerals refer to like parts in which:

Figure 1:
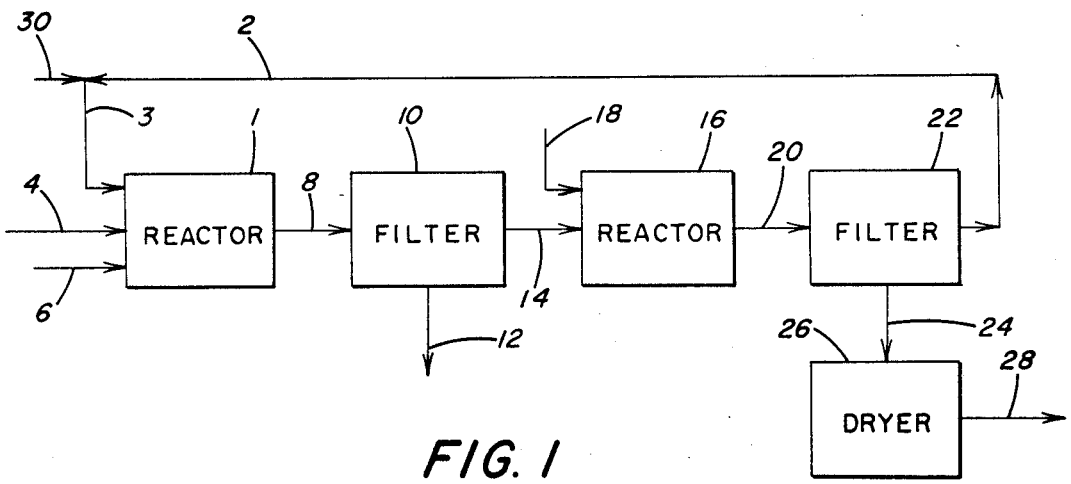
FIG. 1 illustrates diagrammatically one process according to an embodiment of the invention.

Referring now in more detail to FIG. 1, filtrate from filter 22 is introduced to reactor 1 through lines 2 and 3. The filtrate comprises trimethylchlorosilane and methylene chloride. 1H-imidazole is introduced to reactor 1 through line 4 and 1,2-diaminoethane is introduced to the same reactor through line 6. The reaction mixture from reactor 1 is passed through line 8 to filter 10. Solid diaminoethane dihydrochloride is removed through line 12. From filter 10, filtrate comprising 1-(trimethylsilyl)-1H-imidazole and methylene chloride is passed through line 14 to reactor 16. Phosgene is introduced through line 18 to reactor 16. The reaction mixture from reactor 16 is passed through line 20 to filter 22. Solid 1,1'-carbonylbis(1H-imidazole) is removed from filter 22 through line 24 and introduced to dryer 26. Dried 1,1'-carbonylbis(1H-imidazole) is removed from dryer 26 through line 28. Filtrate from filter 22 is introduced to line 2 for recycle to reactor 1. Make-up trimethylchlorosilane and methylene chloride may be introduced as needed to the system at any convenient point, as for example, through line 30.

Figure 2:
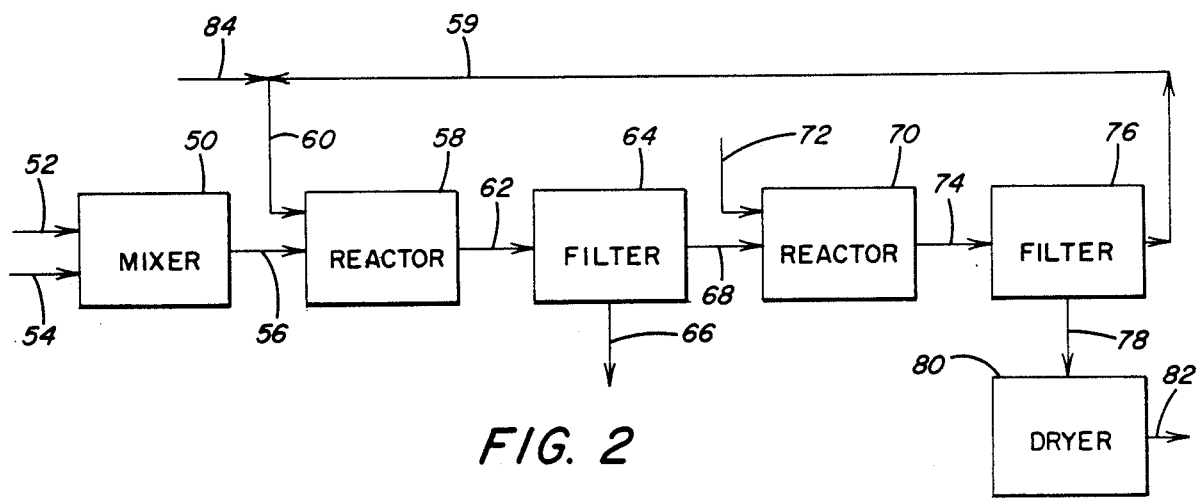
FIG. 2 illustrates diagrammatically another embodiment of the invention.

In FIG. 2, 1H-imidazole is introduced to mixer 50 through line 52 and 1,2-diaminoethane is introduced to mixer 50 through line 54. The mixture from mixer 50 is passed through line 56 to reactor 58. Filtrate from filter 76 is introduced to reactor 58 through lines 59 and 60. The filtrate comprises trimethylchlorosilane and toluene. The reaction mixture from reactor 58 is passed through line 62 to filter 64. Solid diaminoethane dihydrochloride is removed through line 66. From filter 64, filtrate comprising 1-(trimethylsilyl)-1H-imidazole and toluene is passed through line 68 to reactor 70. Phosgene is introduced through line 72 to reactor 70. The reaction mixture from reactor 70 is passed through line 74 to filter 76. Solid 1,1'-carbonylbis(1H-imidazole) is removed from filter 76 through line 78 and introduced to dryer 80. Dried 1,1'-carbonylbis(1H-imidazole) is removed from dryer 80 through line 82. Filtrate from filter 76 is introduced to line 59 for recycle to reactor 58. Make-up trimethylchlorosilane and toluene may be introduced as needed to the system at any convenient point, as for example, through line 84.

Figure 3:
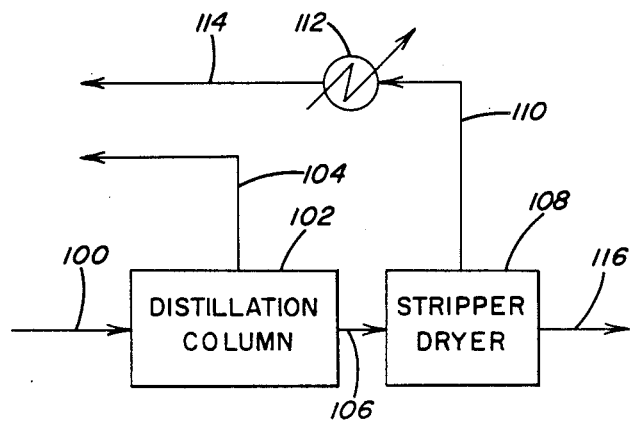
FIG. 3 illustrates diagrammatically a recovery procedure which may be used in lieu of the second filtering step and the drying step of FIG. 1 or FIG. 2.

Referring now to FIG. 3, when the reaction mixture from reactor 16 of FIG. 1 or from reactor 70 of FIG. 2 contains solvent having a higher boiling point than trimethylchlorosilane, such reaction mixture may be passed through line 100 to distillation column 102. Trimethylchlorosilane is removed from distillation column 102 as condensed distillate through line 104 and recycled to reactor 1 of FIG. 1 or reactor 58 of FIG. 2, as the case may be. Bottoms from distillation column 102 are introduced through line 106 to stripper-dryer 108 which is typically operated under vacuum. Solvent vapor is removed from stripper-dryer 110 and introduced to condenser 112 where vapor is condensed. Liquid solvent is removed from condenser 112 through line 114 and recycled to reactor 1 of FIG. 1 or reactor 58 of FIG. 2, as the case may be. Dried 1,1'-carbonylbis(1H-imidazole) is removed from stripper-dryer 108 through line The invention is further described in conjunction with the following examples which are to be considered illustrative rather than limiting. In these examples, all parts are parts by weight and all percentages are percentages by weight unless otherwise specified.

EXAMPLE I

A 50 milliliter single-necked round bottom flask equipped with a magnetic stirring bar was charged sequentially with 3.0 grams of 1,2-diaminoethane and 3.4 grams of 1H-imidazole. The charged materials were stirred and warmed slightly to dissolve the 1H-imidazole. The dropwise addition of 5.6 grams of trimethylchlorosilane produced a highly exothermic, fuming reaction in which solid and liquid phases were formed. Warming on a steam bath while the reaction mixture was protected by a drying tube caused liquification of some of the solid. The sequential addition of 0.4 gram and 1.0 gram quantities of 1,2-diaminoethane caused all of the solid to dissolve. Heating on a steam bath caused no change except for a lowering in the viscosity of the slightly viscous reaction mixture. The reaction mixture was then left to stand overnight at room temperature protected from moisture by the drying tube. No change in composition resulting from standing overnight was observed. One gram of trimethylchlorosilane was added and the reaction was heated a few minutes on the steam bath. Three successive additions of 2 gram quantities of trimethylchlorosilane were made. Each addition was followed by heating the reaction mixture on the steam bath for a few minutes. The reaction mixture that resulted was a yellow liquid over a white crystalline precipitate. Further addition of trimethylchlorosilane produced no change. Gas-liquid chromatographic analysis showed the liquid to contain 1-(trimethylsilyl)-1H-imidazole and trimethylchlorosilane.

EXAMPLE II

A 250 milliliter single-necked round bottom flask equipped with a magnetic stirring bar was charged with 34.0 grams of 1H-imidazole and 102 grams of methylene chloride. The flask was fitted with a condenser and the charged materials were heated to reflux. The 1H-imidazole dissolved to form a clear, slightly colored solution. As the solution cooled to room temperature, 1H-imidazole precipitated. To the slurry was slowly added 59.4 grams of trimethylchlorosilane. An exothermic reaction occurred which heated the reaction mixture to boiling and caused the solid 1H-imidazole to disappear. Upon cooling, some crystallization occurred. A drying tube was attached to the condenser and the reaction mixture was refluxed overnight. The next morning it was observed that a sublimate had formed on the cooler parts of the flask, leaving an almost clear, very light yellow solution. The reaction mixture was allowed to cool to room temperature and then the dropwise addition of 15.3 grams of 1,2-diaminoethane was made. The reaction mixture was stirred overnight. A further 1.0 gram of 1,2-diaminoethane was made dropwise. After standing over the weekend, the reaction mixture was filtered using a sealed frit under nitrogen. A very compact filter cake was formed. The flask and the cake were washed with 30 milliliters of fresh methylene chloride and the washings added to the original filtrate. The mixture was a hazy orange solution weighing 183.0 grams. The filter cake was dried with vacuum on the funnel overnight to a white powdery solid weighing 28.4 grams. Infrared spectroscopy showed the powder to be 1,2-diaminoethane dihydrochloride. Nuclear magnetic resonance spectroscopy showed no detectable 1H-imidazole hydrochloride in the powder. Gas-liquid chromatographic analysis of the orange solution indicated it contained 32.7 weight percent 1-(trimethylsilyl)-1H-imidazole, but it later became clear that the response factor for 1-(trimethylsilyl)-1H-imidazole versus methylene chloride was erroneous. Consequently, although gas-liquid chromatographic analysis shows 1-(trimethylsilyl)-1H-imidazole to be present in substantial amount, the quantitative value of 32.7 weight percent is erroneous.

EXAMPLE III

A 250 milliliter three-necked flask equipped with a magnetic stirring bar, a thermometer, a tube for introduction of phosgene and a Friedrichs condenser, was charged with 183 grams of the orange solution produced in Example II. Phosgene was introduced according to the schedule of Table 1.

TABLE 1

| Time, minutes | Temperature, °C. | COCl$_2$ Charged, grams, cumulative | Remarks |
|---|---|---|---|
| 0 | 40 | 0 | Addition begun. |
| 8 | 24 | 8 | Precipitate Appears |
| 10 | 19 | 10 | |
| 15 | 23 | 15 | Becoming thick with precipitate. |
| 20 | 20 | 20 | Very thick slurry. |
| 23 | 21.5 | 23 | Very thick slurry. |
| 25 | 23 | 25 | Suddenly much thicker. |
| 26 | 21 | 26 | Starting to stir again; addition completed. |
| 28 | 14 | 26 | Much thinner again; stirring slowed to prevent splattering. |

The reaction mixture was cooled to 0° C. It was observed the reaction mixture remained thin. The reaction mixture was filtered cold with a sealed frit under nitrogen. Additional liquid was forced from the filter cake by slightly pressurizing the funnel with nitrogen. The cake was rinsed with 20 milliliters of fresh methylene chloride and additional liquid was forced from the cake by slight nitrogen pressure. The washings were added to the original filtrate to form a liquid mixture. Drying with nitrogen flow was continued until the cake became ice cold. The cake was then dried under vacuum. The resulting freely flowing solid was placed in a dry bag containing nitrogen, sealed and allowed to stand overnight. The solid was again dried for approximately 1 hour under vacuum, then heated to about 60° C. and again dried for approximately 1 hour under vacuum to a fine crystalline powder. The powder was transferred in a dry bag to a bottle and sealed under nitrogen. The bottled product weighed 37.8 grams. Gas-liquid chromatographic analysis showed the powder to contain 99.8 weight percent 1,1'-carbonylbis(1H-imidazole), 0.2 weight percent methylene chloride and less than 0.01 weight percent trimethylchlorosilane.

Immediately after filtering, the liquid mixture was clear. While standing overnight, a very slight quantity of fine brown solids precipitated and settled out of the solution. The liquid mixture weighed 131.4 grams. Gas-liquid chromatographic analysis indicated the liquid mixture contained 36.3 weight percent trimethylchlorosilane.

EXAMPLE IV

A 250 milliliter single-necked flask equipped with a magnetic stirring bar was charged with 131.4 grams of the mother liquor produced in Example III. While the mother liquor was stirred on an ice bath, 34.04 grams of 1H-imidazole was slowly added while a nitrogen blanket was maintained over the flask. An exothermic reaction occurred and the solid 1H-imidazole disappeared; however, the ice bath prevented the reaciton mixture from reaching reflux temperature. After the addition of 1H-imidazole had been completed, the warm reaction mixture was removed from the ice bath and stirred for about 30 minutes. A fine precipitate was observed. The flask was equipped with a Claisen adapter, a reflux condenser, and a 50 milliliter addition funnel. The addition funnel was charged with 15.2 grams of 1,2-diaminoethane. Both the reaction flask and the addition funnel were kept under nitrogen at all times. The 1,2-diaminoethane was added dropwise to the stirred reaction mixture over a period of about 5 minutes. Precipitate formed immediately. The exothermic reaction caused moderate boiling and refluxing after about half the 1,2-diaminoethane had been added. After the addition was completed, the slurry was stirred for about 30 minutes as the temperature slowly declined. An addition of 9.5 grams of trimethylchlorosilane was made at room temperature and the reaction mixture was allowed to stand overnight. Sequential additions of 1.1 grams of 1,2-diaminoethane and 4.6 grams of trimethylchlorosilane were made at room temperature. The reaction mixture was refluxed for 15 minutes and then allowed to settle for 10 minutes. An addition of 1.0 gram of 1H-imidazole was made. About 10 minutes later an addition of 3.2 grams of trimethylchlorosilane was made. About 5 minutes later an addition of 1.5 grams of 1,2-diaminoethane was made. The reaction mixture was allowed to stand for about 10 minutes, refluxed for about 30 minutes, and allowed to stand for about 10 minutes. An addition of 6.8 grams of trimethylchlorosilane was made. The reaction mixture was refluxed for about 30 minutes and then allowed to stand at room temperature overnight. The reaction mixture was filtered under nitrogen, the filter cake was washed with 51.4 grams of fresh methylene chloride, and the washings added to the original filtrate. Inasmuch as the first portion of the filtrate was cloudy, the mixture of original filtrate and washings was refiltered. The resulting filtrate weighed 186.8 grams. Gas-liquid chromatographic analysis of the filtrate indicated it contained 32.8 weight percent 1-(trimethylsilyl)-1H-imidazole. The quantitative value, however, is erroneous for the reasons set forth in Example II. The filter cake, after drying, weighed 38.0 grams.

EXAMPLE V

A 250 milliliter three-necked flask equipped as in Example III was charged with 186.8 grams of the filtrate produced in Example IV. Phosgens was introduced according to the schedule of Table 2.

TABLE 2

| Time, minutes | Temperature, °C. | COCl$_2$ Charged, grams, cumulative | Remarks |
| --- | --- | --- | --- |
| 0 | 0.5 | 0 | Cooling in ice bath; addition begun. |
| 5 | 9 | 5 | |
| 7 | 11.5 | 7 | Precipitate forming. |
| 15 | 20 | 15 | Becoming thick with precipitate. |
| 20 | 16 | 20 | |
| 24 | 18.5 | 24 | Very thick. |
| 26 | 21.5 | 26 | Much thicker; little stirring at sides of flask. |
| 27 | 20 | 27 | Ice bath removed. |
| 28 | 17 | 29 | Addition discontinued. |
| 32 | 15 | 29 | Much thinner. |
| 78 | 15 | 29 | Cooling in ice bath. |

The reaction mixture was filtered cold with a sealed frit under nitrogen. Additional liquid was forced from the filter cake by slightly pressurizing the funnel with nitrogen The cake was rinsed with 99.8 grams of fresh methylene chloride in portions, the reaction flask being rinsed also. The washings were added to the original filtrate to form a liquid mixture. The cake was dried in the manner of Example III. The resulting Powder weighed 41.2 grams. Gas-liquid chromatographic analysis showed the powder to contain 97.9 weight percent 1,1'-carbonylbis(1H-imidazole), 2.0 weight percent imidazole, 0.03 weight percent methylene chloride, and less than 0.02 weight percent trimethylchlorosilane.

Immediately after filtering, the liquid mixture was clear. While standing over the weekend, some solids precipitated and settled out of the solution. The liquid mixture weighed 145.9 grams. Gas-liquid chromatographic analysis indicated the liquid mixture contained 34.6 weight percent trimethylchlorosilane.

EXAMPLE VI

A 250 milliliter single-necked flask equipped with a magnetic stirring bar was charged with 145.9 grams of the mother liquor produced in Example V. The addition of 10.5 grams of trimethylchlorosilane caused some white crystals to precipitate. These settled rapidly. While the reaction mixture was stirred on a cold water bath, 34.04 grams of 1H-imidazole was added over a period of about one minute. Some exotherm occurred, but the reaction mixture did not reflux. After the solid 1H-imidazole had disappeared, a fine precipitate appeared. The reaction mixture was removed from the cold water bath and equipped with a Claisen adapter, a reflux condenser, and a 50 milliliter addition funnel. The addition funnel was charged with 16.0 grams of 1,2-diaminoethane. Both the reaction flask and the addition funnel were kept under nitrogen at all times. The 1,2-diaminoethane was added dropwise over a 20 minute period. Near the end of the addition, refluxing was observed. After being stirred warm for about 15 minutes, the reaction mixture was allowed to settle and cool An addition of 1.4 grams of 1,2 diaminoethane was made. The reaction mixture was refluxed for 10 minutes and then allowed to stand overnight at room temperature. An addition of 0.8 gram of 1,2-diaminoethane was made at room temperature. Seventy minutes later an addition of 1.0 gram of 1,2-diaminoethane was made. Seventy-nine minutes later an addition of 1.0 gram of 1,2-diaminoethane was made. Fifty-seven minutes later an addition of 6.1 grams of trimethylchlorosilane was made. After being stirred at room temperature for 161 minutes, the reaction mixture was refluxed for 30 minutes and allowed to cool. The reaction mixture was filtered under nitrogen, but the filtration proceeded much more slowly than previous runs. The cake was somewhat pasty and became very dense near the frit, almost blocking flow even at the maximum vacuum available and with nitrogen pressure above. Breaking the vacuum and scraping the frit to reslurry the material above the frit had only a temporary effect and allowed some fine solid to enter the filtrate. The very slow filtration took over 30 minutes and was followed by an equally slow wash with 35.9 grams of fresh methylene chloride. The washings added to the original filtrate to form a liquid mixture. The liquid mixture weighed 147.8 grams. Gas-liquid chromatographic analysis of the filtrate indicated in contained 59.8 weight percent methylene chloride 38.2 weight percent 1-(trimethylsilyl)-1H-imidazole, 1.2 weight percent hexamethyldisiloxane, 0.6 weight percent 1H-imidazole and a trace of trimethylchlorosilane. The quantitative value is erroneous for the reasons set out in Example II. The filter cake, after drying, weighed 50.6 grams.

EXAMPLE VII

A 250 milliliter three-necked flask equipped as in Example III was charged with 147.8 grams of the filtrate produced in Example VI. Phosgene was introduced according to the schedule of Table 3.

TABLE 3

| Time, minutes | Temperature, °C. | COCl$_2$ Charged, grams, cumulative | Remarks |
|---|---|---|---|
| 0 | 15 | 0 | Cooling in cold water bath; no ice. Addition began. |
| 5 | 23 | 5 | Reaction mixture clearer than at start. |
| 10 | 23.5 | 10 | |
| 14 | 31 | 14 | Sudden precipitation causes stirring to stop as crystalline mass forms throughout reaction mixture. Increase stirring readily breaks up crystals. |
| 20 | 27 | 20 | |
| 23 | 30.5 | 23 | Very thick slurry. |
| 24 | 31 | 24 | Slurry thinning. |
| 25 | 29 | 25 | Addition completed; remove from water bath |
| 32 | 22 | 26.4 | |
| 55 | 17 | 26.4 | Warm to 35° C. in water bath. |
| 90 | 27 | 26.4 | Cool in ice bath to 0° C. |

The reaction mixture was filtered cold with a sealed frit under nitrogen. Inasmuch as filtration proceeded readily, no vacuum was used; only nitrogen pressure from above was employed. Some of the mother liquor was used to further rinse out the reaction flask. This was followed by a rinse with 46.5 grams of ice-cold methylene chloride in two portions. Nitrogen was used to remove additional liquid from the filter cake. The original filtrate, the rinsings and the additional liquid removed were combined to form a liquid mixture. The filtration funnel containing the cake was placed in a 65° C. oven; no discloration occurred. Vacuum was applied to dry the cake and the oven was turned off. After the oven had cooled to room temperature, the vacuum was broken with nitrogen and the funnel and cake were placed in a dry bag for overnight storage. The cake was dried in the manner of Example III. The resulting powder weighed 36.6 grams. Gas-liquid chromatographic analysis showed the powder to contain 97.1 weight percent 1,1'-carbonylbis(1H-imidazole) and 2.8 weight percent imidazole.

Immediately after filtering, the liquid mixture was somewhat hazy. While standing overnight, some solids precipitated and settled. The liquid mixture weighed 133.1 grams. Gas-liquid chromatographic analysis indicated the liquid mixture contained 43.6 weight percent trimethylchlorosilane.

EXAMPLE VIII

A 1-liter, 4-necked round bottom flask equipped with a blade stirrer, a thermometer, a water-cooled vertical condenser with attached drying tube, and an addition funnel graduated to 250 milliliters, was charged with 136.2 grams of 1H-imidazole, 62.7 grams of 1,2-diaminoethane, and 261.2 grams of toluene. The charged materials are stirred to dissolve most of the 1H-imidazole after which 232.8 grams of trimethylchlorosilane (TMCS) was added from the addition funnel according to the schedule of Table 4.

TABLE 4

| Time, minutes | Temperature, °C. | TMCS in Funnel milliliters | Remarks |
|---|---|---|---|
| 0:00 | 18 | ~275 | |
| 0:05 | 36.5 | 243 | All solids dissolved. |
| 0:11 | 42 | 228 | |
| 0:15 | 52 | 198 | Ice bath applied. |
| 0:20 | 55 | 160 | Trace of solids in lower phase. |
| 0:25 | 54 | 140 | Lower phase white with solids. |
| 0:31 | 53 | 95 | White slurry of solids which settle rapidly. |
| 0:37 | 53 | 34 | Ice bath removed. |
| 0:39 | 56 | 20 | |
| 0:40 | 55.5 | 10 | Insulate with heating mantle; no heat applied. |
| 0:40.5 | 54.5 | 0 | |
| 0:46 | 51.5 | 0 | Stirring discontinued. |
| 0:55 | 46.5 | 0 | Supernatent liquid very slightly hazy. |
| 1:15 | 44 | 0 | Supernatent liquid almost clear yellow solution. Solids seem very fine and settled to a very compact layer. |
| 1:45 | 35 | 0 | Ice bath applied; cool to 18° C. |
| 2:40 | 20 | 0 | Filtered with a sealed frit under nitrogen. |

The filtrate was clear yellow. The flask and the filter cake were washed with 173.8 grams of fresh toluene divided into three portions. Only a slight haze appeared in the washings. The washings were added to the filtrate. The resulting product, which weighed 657.5 grams, was stirred and then allowed to stand quiescently overnight. By the next morning, the haze had settled to form a trace of white solids on the bottom of the container. The solids were too small in quantity to filter. Gas-liquid chromatographic analysis on a first column indicated the liquid contained 2.5 weight percent of a mixture of trimethylchlorosilane and hexamethyldisiloxane, 51.0 weight percent toluene, 1.3 weight percent 1H-imidazole, and 45.0 weight percent 1-(trimethylsilyl)-1H-imidazole. Gas-liquid chromatographic analysis on a second column indicated the liquid contained 1.6 weight percent trimethylchlorosilane, 1.6 weight percent hexamethyldisiloxane, 56.9 weight percent toluene, 3.1 weight percent 1H-imidazole, and 36.8 weight percent 1-(trimethylsilyl)-1H-imidazole. Although these analyses show 1-(trimethylsilyl)-1H-imidazole to be present in substantial amount, the precise quantitative values of both analyses are believed to be unreliable.

The filter cake was dried in a vacuum oven at 65° C. to 70° C. for several hours. Some crystals formed on the door of the vacuum oven. The recovered dry solids weighed 137.2 grams. Wet analysis showed the dried solids to contain 97.2 weight percent 1,2-diaminoethane dihydrochloride, 3.8 weight percent 1H-imidazole hydrochloride, and 0.45 weight percent of total base calculated as 1H-imidazole.

EXAMPLE IX

A 1-liter, 3-necked round bottom flask having a bottom outlet, which flask was equipped with a blade stirrer, a thermometer, and a tube for introduction of phosgene held by a gas venting adapter, was charged with the product (viz., the liquid containing the trace of solids) of Example VIII. The charged material was cooled with an ice bath and phosgene was introduced according to the schedule of Table 5.

TABLE 5

| Time, minutes | Temperature, °C. | COCl$_2$ Charged, grams, cumulative | Remarks |
|---|---|---|---|
| 0:00 | 7 | 0 | Ice bath in place. |
| 0:05 | 13.5 | 7.4 | |
| 0:09 | 15.5 | 13.6 | Hazy with fine solids. |
| 0:16 | 23 | 23.3 | |
| 0:25 | 17.5 | 37.0 | |
| 0:40 | 18 | 60.3 | |
| 0:50 | 15 | 75.9 | |
| 1:00 | 19.5 | 91.3 | |
| 1:02 | 20 | 94.4 | Very thick slurry. |
| 1:04 | 19.5 | 97.7 | |
| 1:05 | 18.5 | 99.4 | COCl$_2$ addition terminated. |
| 1:06 | 18 | 99.4 | Reaction mixture thinning. Ice bath removed. Stirring stopped. |

The solids of the reaction mixture settled slowly to reveal a cloudy but colorless supernatent liquid layer and a large layer of white solids. The increase in the weight of the reaction mixture due to phosgenation was 97.8 grams.

After agitating to redisperse the solids, 275.1 grams of the reaction mixture was drawn from the bottom outlet of the reaction flask and charged into a 500 milliliter round bottom stripping flask under nitrogen. The liquid of the withdrawn portion was removed on a rotary evaporator under vacuum. The maximum drying temperature of the solids remaining in the rotary evaporator was 85° C. The solids were broken up to form a first product which weighed 58.4 grams and was an off-white powder. Wet analysis showed the first product to contain 2.33 weight percent 1H-imidazole hydrochloride and gas-liquid chromatographic analysis showed the first product to contain 0.14 weight percent toluene. Wet analysis also indicated that the first product contained 84.3 weight percent 1,1'-carbonylbis(1H-imidazole), but while the analysis is believed correct insofar as it shows a substantial amount of 1,1'-carbonylbis(1H-imidazole) to be present, the quantitative value is now regarded as unreliable. The distillate removed during the stripping weighed 176.4 grams. Gas-liquid chromatographic analysis showed the distillate to contain 25.9 weight percent trimethylchlorosilane, 2.2 weight percent hexamethyldisiloxane, and 71.9 weight percent toluene.

The reaction mixture which remained in the reaction flask was subjected to vacuum distillation at an absolute pressure of about 51 kilopascals in a three-bulb Snyder column according to the schedule of Table 6.

TABLE 6

| Time, hours:minutes | Pot Temperature, °C. | Head Temperature °C. | Remarks |
|---|---|---|---|
| 0:00 | 58 | 36.5 | First distillate over. Very thick slurry |
| 0:08 | 60 | 40 | |
| 0:28 | 64.5 | 39 | |
| 0:38 | 67 | 40.5 | |
| 0:48 | 69.5 | 40 | |
| 1:03 | 74.5 | 40.5 | Thick orange slurry. |
| 1:23 | 80.5 | 40.5 | Slurry darker orange and thinning. |
| 1:33 | 82.5 | 41 | |
| 1:38 | 84 | 55 | Much thinner slurry; brown-orange. |
| 1:48 | 86 | 70 | |
| 1:53 | 86.5 | 82 | Distillation discontinued, Vacuum broken with nitrogen Heating continued at ambient pressure under nitrogen. |
| 2:03 | 97 | | Solids are dissolving. |
| 2:08 | 100 | | Most solids dissolved. |
| 2:10 | 100.7 | | Yellow solution forms. A tar separates suddenly A few large pieces of solid not yet dissolved. |
| 2:18 | 105.5 | | Stirring discontinued. |

The distillate which was removed weighed 147.2 grams. Gas-liquid chromatographic analysis showed this distillate to contain 90.7 weight percent trimethylchlorosilane, 2.7 weight percent hexamethyldisiloxane, and 6.6 weight percent toluene.

The heavy tar-like phase which settled out of the yellow solution after stirring was discontinued was removed through the bottom outlet together with a small quantity of yellow solution. The removed material weighed 6.4 grams.

A 1-liter, 1-necked round bottom flask containing 20 milliliters of toluene and equipped with a magnetic stirring bar, a drying tube, and an electric heating mantle, was heated until the toluene refluxed all the way to the joint where the drying tube was attached to the flask. Heating was discontinued and the drying tube was removed. The hot solution remaining in the pot of the distillation apparatus was drawn from the bottom outlet and charged under nitrogen into the hot flask containing the toluene. The drying tube was replaced. While stirring vigorously, crystals formed, rapidly at first, then slower as the mixture cooled further on standing in the room. As the mixture cooled, air was permitted to enter the flask through the drying tube. A very thick but uniform slurry of off-white crystals formed which settled rapidly when stirring was discontinued to reveal a clear, very light green supernatant liquid. The mixture was allowed to stand quiescently overnight. The next day the mixture was stirred for about one hour to redisperse the solids. After standing quiescently, the supernatant liquid did not become as clear as before. Gas-liquid chromatographic analysis showed the slightly hazy supernatant liquid to contain 0.1 weight percent trimethylchlorosilane, 1.0 weight percent hexamethyldisiloxane, 98.8 weight percent toluene and 0.09 weight percent of an unknown which may have been phosgene. After the mixture in the flask was stirred to redisperse the solids, the liquid was removed on a rotary evaporator under vacuum. The maximum drying temperature of the solids remaining in the rotary evaporator was 82° C. The solids were broken up to form a second product which weighed 98.2 grams and was an off-white powder. Wet analysis showed the second product to contain 0.28 weight percent 1H-imidazole hydrochloride, while gas-liquid chromatographic analysis showed the second product contained less than 0.01 weight percent toluene. Coulometric carbon dioxide titration showed the second product to contain 97.0 weight percent 1,1'-carbonylbis(1H-imidazole), a value which is regarded as reliable.

EXAMPLE X

A 500 cubic centimeter, 4-necked round bottom flask equipped with a stirrer, a thermometer, a water-cooled vertical condenser with a bubble tube fitted to the exit part of the condenser, and an addition funnel fitted with an inlet port for the introduction of nitrogen, was charged with 56.11 grams of 1-(trimethylsilyl)-1H-imidazole of about 96% purity and 168.3 cubic centimeters of methylene chloride. Stirring was begun and the charged materials were cooled to about 5° C. while under a positive nitrogen pressure. The addition funnel was charged with 23.00 grams of thiophosgene of about 93% purity. A steady dropwise addition of the thiophosgene was begun. An immediate exotherm took place and the temperature of the reaction mixture rose to about 18° C. within a few minutes. Further cooling was applied to maintain the temperature in the range of 15° C. to 20° C. during the remainder of the addition. The addition was completed approximately 25 minutes after it was begun. The reaction mixture was then stirred at ambient temperature for one hour. At this point, the reaction mixture was a clear yellow solution. The trimethylchlorosilane which had been produced and the methylene chloride were removed from the reaction mixture in a Buchi rotating evaporator under the vacuum provided by a water aspirator. The yellow solids which remained were heated with a warm water bath while turning the evaporator under vacuum for an additional hour. The flask containing the solids was then released, capped, and transferred to a glove bag under nitrogen. The yellow solids were placed in a mortar and pulverized with a pestle. The resulting product, which weighed 35.28 grams, was bottled under nitrogen. The yield of the product was 99.0% based on 1-(trimethylsilyl)-1H-imidazole. Nuclear magnetic resonance spectroscopy confirmed the structure of the product as that of 1,1'-thiocarbonylbis(1H-imidazole). The product was analyzed for 1H-imidazole hydrochloride by wet analysis. Found: 2.40%, 2.46% 1H-imidazole hydrochloride. Average Found: 2.43% 1H-imidazole hydrochloride. The product was analyzed for purity by gas-liquid chromatography. Found: 96.63%, 96.49% 1,1'-thiocarbonylbis (1H-imidazole) by weight. Average Found: 96.56% 1,1'-thiocarbonylbis (1H-imidazole) by weight. The same gas-liquid chromatographic analysis showed a peak for 1H-imidazole. When this is corrected for the hydrochloride based on the assumption that all 1H-imidazole hydrochloride is converted to free 1H-imidazole during the analysis, the result was 0.0 weight percent 1H-imidazole. Another gas-liquid chromatographic analysis showed no detectable thiophosgene or carbon tetrachloride in the product. The results of elemental analysis are shown in Table 7.

TABLE 7

|  | % C | % H | % N | % S |
|---|---|---|---|---|
| Found | 46.94 | 3.42 | 31.35 | 18.02 |
|  | 46.97 | 3.44 | 31.21 | 18.18 |
| Average Found | 46.96 | 3.43 | 31.28 | 18.15 |
| Theory | 47.18 | 3.40 | 31.45 | 17.99 |

Although there is still uncertainty in respect of the quantitative accuracy of the gas-liquid chromatographic methods, this example shows that a reasonably pure product has been made based on an only 93% purity of the thiophosgene used.

Although the present invention has been described with reference to specific details of certain embodiments thereof, it is not intended that such details should be regarded as limitations upon the scope of the invention except insofar as they are included in the accompanying claims.

I claim:
1. A method comprising reacting
   (a) at least one 1-unsubstituted 1H-azole compound selected from 1-unsubstituted monocyclic 1H-diazole compounds, 1-unsubstituted bicyclic 1H-diazole compounds containing a fused benzene ring, 1-unsubstituted monocyclic 1H-triazole compounds, and 1-unsubstituted bicyclic 1H-triazole compounds containing a fused benzene ring,
   (b) at least one substituted silane represented by the formula $R_1R_2R_3SiX$, and
   (c) at least one primary amine wherein said primary amine is $\alpha,\omega$-diamino-n-alkane having from 2 to about 12 carbon atoms,
to form at least one 1-$(R_1R_2R_3Si)$ substituted 1H-azole compound which principally accumulates in a liquid phase and to form hydrohalide salt of said primary amine which principally accumulates in at least one phase which is different from said liquid phase, wherein $R_1$, $R_2$, and $R_3$ are each independently lower alkyl or phenyl and wherein X is fluoro, chloro, bromo, or iodo.

2. The method of claim 1 wherein said liquid phase is substantially separated from the different phase or phases.

3. The method of claim 2 wherein said hydrohalide salt principally accumulates in one phase which is different from said liquid 4. The method of claim 3 wherein the different phase is a solid phase.

5. The method of claim 4 wherein the reaction is conducted in the presence of inert solvent.

6. The method of claim 5 wherein said 1-unsubstituted 1H-azole compound is 1H-imidazole, 1H-1,2,4- triazole, 3,5-dimethyl-1H-pyrazole, 1H-benzimidazole, or 1H-benzotriazole.

7. The method of claim 5, wherein
   (a) said 1-unsubstituted 1H-azole compound is 1H-imidazole,
   (b) said substituted silane is trimethylchlorosilane, and
   (c) said 1-($R_1R_2R_3$Si) substituted azole is 1-(trimethylsilyl)-1H-imidazole.

8. The method of claim 7 wherein said inert solvent is methylene chloride or toluene.

9. A cyclic process comprising:
   (a) reacting in the presence of inert solvent,
      (i) at least one 1-unsubstituted 1H-azole compound selected from 1-unsubstituted monocyclic 1H-diazole compounds, 1-unsubstituted bicyclic 1H-diazole compounds containing a fused benzene ring, 1-unsubstituted monocyclic 1H-triazole compounds, and 1-unsubstituted bicyclic 1H-triazole compounds containing a fused benzene ring,
      (ii) at least one substituted silane represented by the formula $R_1R_2R_3$SiX, and
      (iii) at least one primary amine wherein said primary amine is α,ω-diamino-n-alkane having from 2 to about 12 carbon atoms, to form at least one 1-($R_1R_2R_3$Si) substituted 1H-azole compound which principally accumulates in a liquid phase and to form hydrohalide salt of said primary amine which principally accumulates in at least one phase which is different from said liquid phase,
   (b) substantially separating said liquid phase from the different phase or phases,
   (c) reacting at least a portion of said 1-($R_1R_2R_3$Si) substituted 1H-azole compound with at least one member of the group consisting of

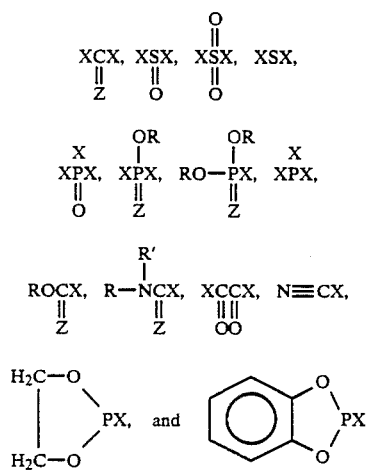

to form a reaction mixture comprising said inert solvent, said substituted silane, and material selected from
      (i) product compound formed by the replacement of at least one X of said member with a 1H-azol-1-yl group,
      (ii) dissociation products of said product compound, and
      (iii) a mixture thereof,
   (d) substantially separating the substituted silane produced in step (c) from said product compound or at least one dissociation product of said product compound, and
   (e) recycling said separated substituted silane to the reaction of step (a),
wherein: $R_1$, $R_2$, and $R_3$ are each independently lower alkyl or phenyl; each R is independently lower alkyl, unsubstituted phenyl, phenyl substituted by from 1 to 3 halo groups, phenyl substituted by from 1 to 3 lower alkyl groups, ortho-nitrophenyl, para-nitrophenyl; each R' is independently hydrogen or R; each Z is independently oxygen or sulfur; and each X is independently fluoro, chloro, or bromo.

10. The cyclic process of claim 9 wherein said primary amine is a α,ω-diamino-n-alkane having from about 2 to about 4 carbon atoms.

11. The cyclic process of claim 9 wherein said primary amine is 1,2-diaminoethane.

12. The cyclic process of claim 11 wherein said hydrohalide salt principally accumulates in one phase which is different from said liquid phase.

13. The cyclic process of claim 12 wherein the different phase is a solid phase.

14. The cyclic process of claim 8 wherein said product comprises at least one compound in which each X of substantially all of said member has been replaced with a 1H-azol-1-yl group.

15. The cyclic process of claim 9 wherein said member is phosgene.

16. The cyclic process of claim 15 wherein said 1-unsubstituted 1H-azole compound is 1H-imidazole, 1H-1,2,4-triazole, 3,5-dimethyl-1H-pyrazole, 1H-benzimidazole, or 1H-benzotriazole.

17. The cyclic process of claim 15 wherein said substituted silane is trimethylchlorosilane.

18. The cyclic process of claim 17 wherein said 1-unsubstituted 1H-azole compound is 1H-imidazole, said 1-($R_1R_2R_3$Si) substituted 1H-azole compound is 1-(trimethylsilyl)-1H-imidazole, and said product compound is 1,1'-carbonylbis(1H-imidazole).

19. The cyclic process of claim 16 wherein said inert solvent is methylene chloride or toluene.

20. The method of claim 1 wherein said primary amine is α,ω-diamino-n-alkane having from 2 to about 4 carbon atoms.

21. The method of claim 1 wherein said primary amine is 1,2-diaminoethane.

* * * * *